(12) United States Patent
Jung (10) Patent No.: US 8,292,936 B2
(45) Date of Patent: Oct. 23, 2012

(54) NECK APPARATUS AND METHODS OF USING THE SAME

(76) Inventor: Ji Hyuk Rick Jung, Alpharetta, GA (US)

( * ) Notice: Subject to any disclaimer, the term of this patent is extended or adjusted under 35 U.S.C. 154(b) by 269 days.

(21) Appl. No.: 12/567,073

(22) Filed: Sep. 25, 2009

(65) Prior Publication Data

US 2010/0198323 A1    Aug. 5, 2010

Related U.S. Application Data

(60) Provisional application No. 61/100,076, filed on Sep. 25, 2008.

(51) Int. Cl.
*A61F 7/00* (2006.01)
*A41B 3/04* (2006.01)
(52) U.S. Cl. ............... 607/109; 2/129; 2/132; 2/207
(58) Field of Classification Search ............. 607/109; 2/129, 132, 207
See application file for complete search history.

(56) References Cited

U.S. PATENT DOCUMENTS

| | | | | |
|---|---|---|---|---|
| 1,473,506 A * | 11/1923 | Nessler | ............ | 607/109 |
| 1,567,931 A * | 12/1925 | Epler | ............ | 607/112 |
| 1,616,961 A * | 2/1927 | Carter | ............ | 607/109 |
| 1,910,328 A * | 5/1933 | Glennan | ............ | 607/109 |
| 2,071,706 A * | 2/1937 | Reach | ............ | 607/112 |
| 2,134,473 A * | 10/1938 | Engelson | ............ | 2/102 |
| 2,250,840 A * | 7/1941 | Pomeranz | ............ | 607/109 |
| 2,562,121 A * | 7/1951 | Poux | ............ | 165/46 |
| 2,870,448 A * | 1/1959 | Rosenthal | ............ | 2/91 |
| 3,506,013 A * | 4/1970 | Zdenek | ............ | 607/108 |
| 3,748,661 A * | 7/1973 | Smith | ............ | 2/207 |
| 3,889,684 A * | 6/1975 | Lebold | ............ | 607/109 |
| 4,576,169 A * | 3/1986 | Williams | ............ | 607/109 |
| 4,586,506 A * | 5/1986 | Nangle | ............ | 607/112 |
| 4,641,655 A * | 2/1987 | Abt | ............ | 607/109 |
| 4,742,827 A * | 5/1988 | Lipton | ............ | 607/109 |
| 4,745,922 A * | 5/1988 | Taylor | ............ | 607/104 |
| 4,805,619 A * | 2/1989 | Swearingen | ............ | 607/109 |
| 4,832,030 A * | 5/1989 | De Canto | ............ | 607/109 |
| 4,891,501 A * | 1/1990 | Lipton | ............ | 607/110 |
| 5,072,598 A * | 12/1991 | Dibrell | ............ | 62/259.3 |
| 5,088,549 A * | 2/1992 | Schneider | ............ | 165/46 |
| 5,211,623 A * | 5/1993 | Sarkozi | ............ | 602/18 |
| 5,233,704 A * | 8/1993 | Booher | ............ | 2/207 |
| 5,247,928 A * | 9/1993 | Stilts, Jr. | ............ | 607/109 |
| 5,265,669 A * | 11/1993 | Schneider | ............ | 165/46 |
| 5,295,949 A * | 3/1994 | Hathaway | ............ | 602/18 |
| 5,302,806 A * | 4/1994 | Simmons et al. | ............ | 219/211 |
| 5,400,617 A * | 3/1995 | Ragonesi et al. | ............ | 62/530 |
| 5,484,448 A * | 1/1996 | Steele et al. | ............ | 607/108 |
| 5,507,793 A * | 4/1996 | Hodges | ............ | 607/109 |
| 5,591,122 A * | 1/1997 | Yewer, Jr. | ............ | 602/19 |
| 5,605,144 A * | 2/1997 | Simmons et al. | ............ | 126/204 |
| 5,682,619 A * | 11/1997 | Griffin | ............ | 2/326 |
| 5,697,962 A * | 12/1997 | Brink et al. | ............ | 607/108 |
| 5,728,146 A * | 3/1998 | Burkett et al. | ............ | 607/109 |
| 5,735,889 A * | 4/1998 | Burkett et al. | ............ | 607/96 |

(Continued)

*Primary Examiner* — Roy Gibson
*Assistant Examiner* — Kaitlyn Smith
(74) *Attorney, Agent, or Firm* — J. Clinton Wimbish; Smith Moore Leatherwood LLP (57) ABSTRACT

In one aspect, the present invention provides a neck cooling or heating apparatus comprising a primary band comprising a first end, a second end and a neck cooling or neck heating region positioned between the first end and the second end, the neck cooling or the neck heating region having coupled thereto a tissue cooling or a tissue heating material.

17 Claims, 7 Drawing Sheets

U.S. PATENT DOCUMENTS

| | | | |
|---|---|---|---|
| 5,813,954 A * | 9/1998 | Wilkinson | 482/124 |
| 6,004,345 A * | 12/1999 | Sudsina et al. | 607/108 |
| 6,102,937 A * | 8/2000 | Cramer et al. | 607/109 |
| 6,123,717 A * | 9/2000 | Davis et al. | 607/109 |
| 6,537,235 B1 * | 3/2003 | Connor et al. | 601/70 |
| 6,755,852 B2 * | 6/2004 | Lachenbruch et al. | 607/114 |
| 6,972,029 B2 * | 12/2005 | Mayrhofer et al. | 607/114 |
| 2002/0052569 A1 * | 5/2002 | Horning | 602/41 |
| 2003/0135908 A1 * | 7/2003 | Turkheimer | 2/80 |
| 2006/0010569 A1 * | 1/2006 | Tawfik | 2/207 |
| 2007/0032848 A1 * | 2/2007 | Bridges | 607/114 |
| 2007/0033706 A1 * | 2/2007 | Kuhlmann | 2/207 |
| 2007/0213794 A1 * | 9/2007 | Lauver | 607/109 |
| 2007/0225782 A1 * | 9/2007 | Taylor | 607/108 |
| 2007/0270925 A1 * | 11/2007 | Levinson | 607/108 |
| 2008/0289351 A1 * | 11/2008 | Taylor | 62/259.3 |
| 2009/0133192 A1 * | 5/2009 | Hassell et al. | 5/639 |
| 2009/0222071 A1 * | 9/2009 | Li et al. | 607/114 |
| 2009/0264970 A1 * | 10/2009 | Mickel | 607/108 |
| 2010/0305669 A1 * | 12/2010 | Sasaki | 607/109 |

* cited by examiner

NECK APPARATUS AND METHODS OF USING THE SAME

RELATED U.S. APPLICATIONS

The present application claims priority under 35 U.S.C. §119(e) to U.S. Provisional Patent Application Ser. No. 61/100,076, filed Sep. 25, 2008, which is hereby incorporated by reference in its entirety.

FIELD OF THE INVENTION

The present invention relates to apparatus and methods for cooling or heating parts of the human body and, in particular, to apparatus and methods for cooling or heating the neck.

BACKGROUND OF THE INVENTION

Heat and cold packs are commonly applied to various areas of the human body to relieve a variety of ailments including muscle strains, muscle soreness, and tissue swelling. Moreover, heat and cold packs are also used for general comfort, such as keeping an individual warm in a cold environment or cooling one or more parts of an individual's body experiencing heat related distresses.

In order to maximize the effectiveness and convenience of heat and cold packs, a number of apparatus, such as wraps, have been developed to hold the heat or cold pack in position. Leg wraps, torso wraps and wrist wraps are common apparatus for holding a heat or cold pack in the desired position. In addition to these, neck wraps have also been developed for positioning a heat or cold pack around an individual's neck.

The neck is an increasingly sensitive area that can benefit greatly from application of a heat or cold pack. Currently available apparatus for positioning a heat or cold pack around the neck of an individual, however, can significantly restrict movement of the individual and are generally uncomfortable. U.S. Pat. No. 5,295,949, for example, provides a neck apparatus that encircles or encloses the neck of a user like a collar (e.g. FIG. 7). Such an arrangement is restrictive to head and neck movement and can result in injury if pulled by an external force. As a result, neck apparatus that encircle the neck cannot be used by athletes in contact sports or other individuals at risk of having the neck apparatus pulled upon. Furthermore, an encircling neck apparatus cannot be worn for an extended period of time without experiencing significant discomfort.

SUMMARY

The present invention provides neck apparatus operable to position a heat or cold pack on the neck without the foregoing disadvantages of restricting head and neck movement and the general discomfort of associated with previous apparatus. The non-restrictive nature of neck apparatus of the present invention permits use in a variety of applications, including commercial applications, recreational applications and therapeutic applications. Moreover, neck apparatus of the present invention, in some embodiments, do not completely encircle or enclose the neck, thereby allowing the apparatus to be worn in athletic or other contact situations.

In one aspect, the present invention provides a neck cooling or neck heating apparatus comprising a primary band comprising a first end, a second end and a neck cooling or neck heating region positioned between the first end and the second end, the neck cooling or the neck heating region having coupled thereto a tissue cooling or a tissue heating material. The first end of the primary band comprises a first fastener, and the second end of the primary band comprises a second fastener, wherein the first and second fasteners are adapted to couple to an article of clothing on the torso or waist of an individual. In some embodiments, the primary band does not enclose the neck of the individual and only partially encircles the neck of the individual.

In another aspect, the present invention provides methods of cooling or heating the neck of an individual comprising providing a primary band comprising a first end, a second end and a neck cooling or neck heating region positioned between the first end and the second end, coupling a tissue cooling or tissue heating material to the neck cooling or neck heating region, positioning the tissue cooling or tissue heating material adjacent to the neck of an individual and coupling the first end and the second end of the primary band to an article of clothing on the torso or waist of the individual. In some embodiments, the primary band does not enclose the neck of the individual and only partially encircles the neck of the individual.

These and other embodiments of the present invention are described in greater detail in the detailed description which follows.

DETAILED DESCRIPTION

The present invention provides neck apparatus operable to position a heat or cold pack on the neck of an individual without the foregoing disadvantages of restricting head and neck movement and the general discomfort of associated with previous apparatus. The non-restrictive nature of neck apparatus of the present invention permits use in a variety of applications, including commercial applications, recreational applications and therapeutic applications. Moreover, neck apparatus of the present invention, in some embodiments, do not completely encircle or enclose the neck, thereby allowing the apparatus to be worn in athletic or other contact situations.

In one embodiment, the present invention provides a neck cooling or neck heating apparatus comprising a primary band comprising a first end, a second end and a neck cooling or neck heating region positioned between the first end and the second end, the neck cooling or the neck heating region having coupled thereto a tissue cooling or a tissue heating material. The first end of the primary band comprises a first fastener and the second end of the primary band comprises a second fastener, wherein the first and second fasteners are adapted to couple to an article of clothing on the torso or waist of an individual. In some embodiments, the primary band does not enclose the neck of the individual. In not enclosing the neck, in some embodiments, the primary band contacts the back and/or sides of the neck to provide a tissue cooling or tissue heating material to the back and/or sides of the neck.

Figure 1:
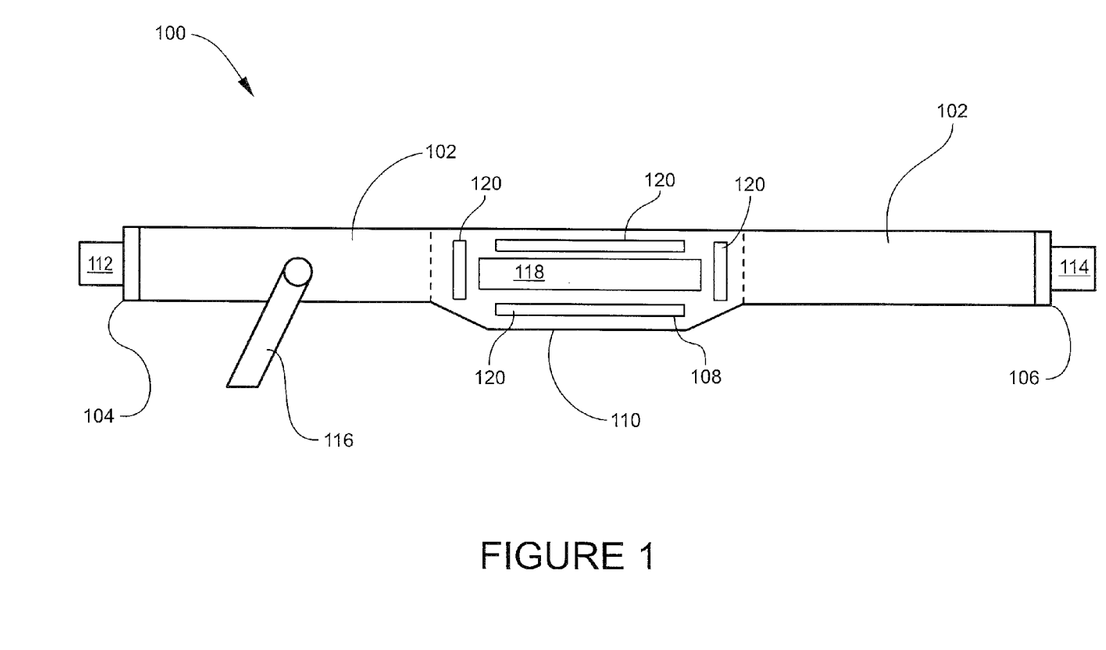
FIG. 1 is a perspective view of a neck cooling or neck heating apparatus according to one embodiment of the present invention.

Turning now to the figures, FIG. 1 illustrates a perspective view of a primary band of a neck cooling or neck heating apparatus according to one embodiment of the present invention. As illustrated in FIG. 1, the primary band (102) of the neck cooling or neck heating apparatus (100) comprises a continuous piece of material having a first end (104) and a second end (106). A neck cooling or neck heating region (108) is positioned between the first end (104) and the second end (106) of the primary band (102). In other embodiments, the primary band is not a continuous piece of material. In one embodiment, for example, the primary band comprises a plurality of individual pieces of material sewn together or otherwise coupled.

When in use, a tissue cooling material or a tissue heating material (118) is coupled to the neck cooling or neck heating region (108). In some embodiments, the tissue cooling or tissue heating material is coupled to the neck cooling or neck heating region (108) of the primary band by at least one hook and loop fastener arrangement. Typical hook and loop fasteners, in some embodiments, comprise VELCRO® or unbreakable loop backings (UBL). In other embodiments, the tissue cooling or tissue heating material is coupled to the neck cooling or neck heating region (108) by a zipper arrangement. In some embodiments, the neck cooling or neck heating region (108) of the primary band (102) comprises a pouch (not shown) in which the tissue cooling or tissue heating material is disposed. The walls of the pouch, in some embodiments, have a variable thickness thereby allowing a user to tailor the amount of cooling or heating tissue of the neck receives from the tissue cooling or tissue heating material.

In some embodiments, the tissue cooling or tissue heating material is reversibly coupled to the primary band (102). In being reversibly coupled, the tissue cooling or tissue heating material can be replaced by a fresh tissue cooling or tissue heating material at any desired time by the individual.

In the embodiment illustrated in FIG. 1, the primary band (102) further comprises a flange or tongue (110). The flange (110) can assist in keeping the neck cooling or neck heating region (108) of the primary band (102) in the proper position when in use by an individual. The flange (110) can be inserted under the shirt or other article of clothing of an individual to assist in maintaining the proper position of the neck cooling or neck heating region (108). The flange (110) can have any desired shape including circular, semicircular, elliptical, triangular, square, rectangular, trapezoidal or any other polygon.

The first end (104) of the primary band (102) illustrated in FIG. 1 comprises a first fastener (112), and the second end (106) of the primary band (102) comprises a second fastener (114). The first (112) and second (114) fasteners are operable to fasten to an article of clothing on the torso or waist of an individual using the neck cooling or neck heating apparatus (100). The first (112) and second (114) fasteners can comprise any fastening means known to one of skill in the art. In one embodiment, for example, the first (112) and second (114) fasteners comprise clamps or clips. In another embodiment, the first (112) and second (114) fasteners comprise hook and loop fasteners, buttons or snap arrangements.

The primary band (102) displayed in FIG. 1 further comprises a cross-member (116). The cross-member (116) is adapted to couple a section of the primary band (102) on one side of the neck cooling or neck heating region (108) with a section of the primary band (102) on the opposite side of the neck cooling or neck heating region (108). In being operable to couple sections of the primary band (102) on opposing sides of the neck cooling or neck heating region (108), the cross-member, in some embodiments, can tighten or loosen the primary band (102) thereby assisting in maintaining the proper positioning of the neck cooling or neck heating region (108) on an individual's neck. In some embodiments, the cross-member couples opposing sides of the primary band by at least one hook and loop fastening arrangement. Moreover, in some embodiments, the cross-member (112) is operable to rotate 360° relative to the primary band (102).

The cross-member (116) can be coupled to the primary band (102) by any means not inconsistent with the objectives of the present invention. In some embodiments, the cross-member (116) is coupled to the primary band (102) by a snap arrangement. A snap arrangement, in some embodiments, can facilitate rotation of the primary band 360° relative to the primary band (102). In another embodiment, the cross-member (116) can be coupled to the primary band (102) by a button arrangement.

The cross-member (116), in some embodiments, is reversibly coupled to the primary band (102). In being reversibly coupled, the cross-member (116) can be detached from the primary band (102).

In some embodiments, a surface of the primary band (102) further comprises one or more bumps, protrusions or ridges (120) operable to facilitate positioning of the tissue cooling or tissue heating material at the desired location on the neck of an individual. In some embodiments, the one or more bumps, protrusions of ridges (120) is disposed in the neck cooling or neck heating region (108).

Figure 2:
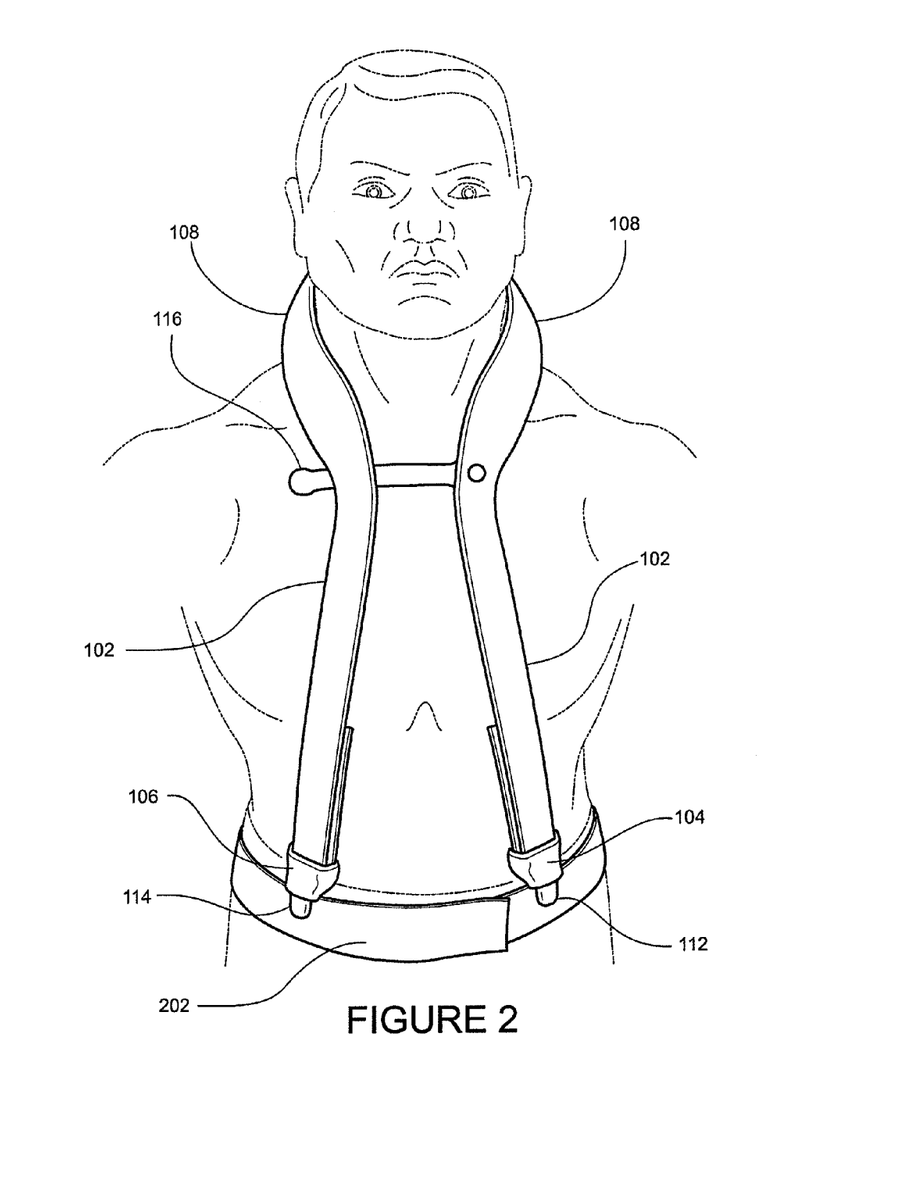
FIG. 2 is a frontal view of a neck cooling or neck heating apparatus applied to the neck of an individual according to one embodiment of the present invention.

FIG. 2 is a frontal view of a the primary band (102) of FIG. 1 applied to the neck of an individual according to one embodiment of the present invention. As illustrated in FIG. 2, the first end (104) and the second end (106) of the primary band (102) are fastened to an article of clothing (202) on the waist of the individual by the first and second fasteners (112, 114), the article of clothing comprising the waistline of pants or shorts. The cross-member (116) couples sections of the primary band (102) on opposing sides of the neck cooling or neck heating region (108). As provided herein, the cross-member (116), in some embodiments, tightens or loosens the primary band (102) along the back and/or sides of an individual's neck thereby assisting in maintaining the proper positioning of the neck cooling or neck heating region (108) on an individual's neck. Additionally, in the embodiment illustrated in FIG. 2, the primary band (102) does not completely encircle or enclose the neck of the individual. Moreover, use of the cross-member (116) does not completely encircle or enclose the neck of the individual.

A tissue cooling or tissue heating material (118) is coupled to the neck cooling or neck heating region (108) and resides between the skin of the individual and the primary band (102).

Figure 3:
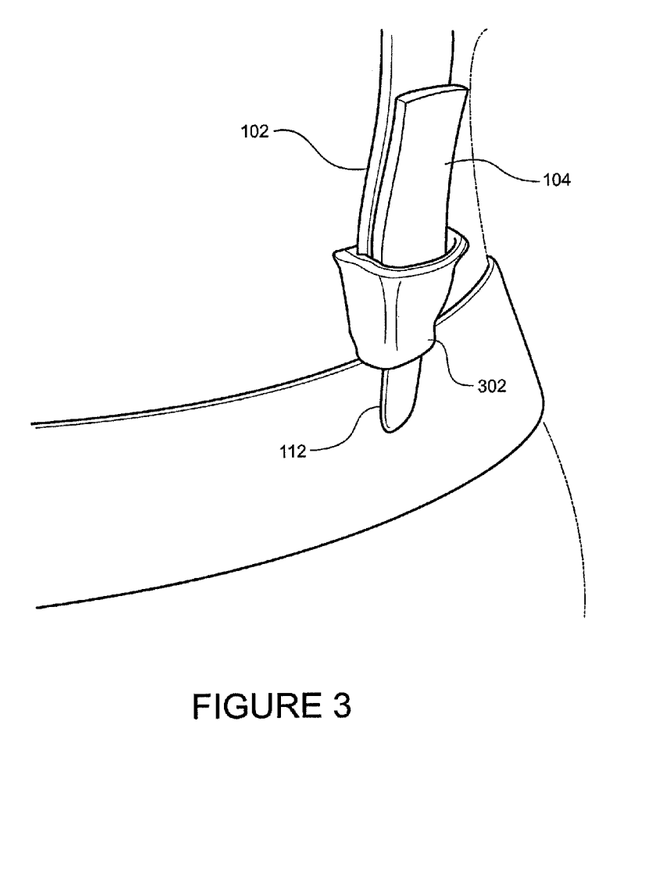
FIG. 3 is a perspective view of a first end of the primary band of a neck cooling or neck heating apparatus fastening to an article of clothing on the waist of an individual.
Figure 7:
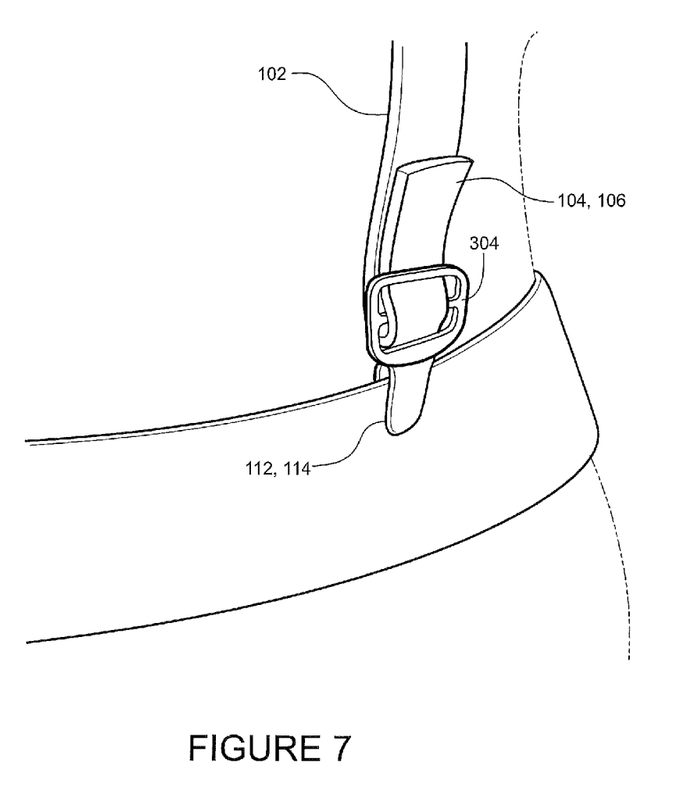
FIG. 7 is a perspective view of a first or second end of the primary band of a neck cooling or neck heating apparatus fastening to an article of clothing on the waist of an individual.

FIG. 3 is a perspective view of the first end (104) of the primary band (102) illustrated in FIG. 1 fastened by a first fastener (112) to an article of clothing around the waist of an individual. The first fastener (112) in the embodiment shown in FIG. 3 comprises a clamp. The clamp is coupled to the first end (104) of the primary band (102) by a loop (not shown) through which the primary band (102) is drawn. The primary band (102) subsequently secures back to itself through at least one hook and loop engagement. A fastener engaging the primary band (102) by a loop, in some embodiments, facilitates adjustment of the length of the primary band (102) thereby providing the proper fit of the primary band (102) on an individual's body. A fastener engaging the primary band (102) by a loop, in some embodiments, facilitates adjustment of tension in the primary band to fit individuals of varying size. In the embodiment shown in FIG. 3, a padding (302) is provided over the loop of the first fastener (112) to prevent irritation resulting from friction between the loop and the body of an individual. In the embodiment shown in FIG. 7, the padding is not shown. FIG. 7 is a perspective view of a first or second end (104, 106) of the primary band (102) of FIG. 1 fastened by a first or second fastener (112, 114) to an article of clothing around the waist of an individual. As in FIG. 3, the first or second fastener (112, 114) in the embodiment shown in FIG. 7 comprises a clamp. The clamp is coupled to the first or second end (104, 106) of the primary band (102) by a loop (304) through which the primary band (102) is drawn, as described above.

Figure 4:
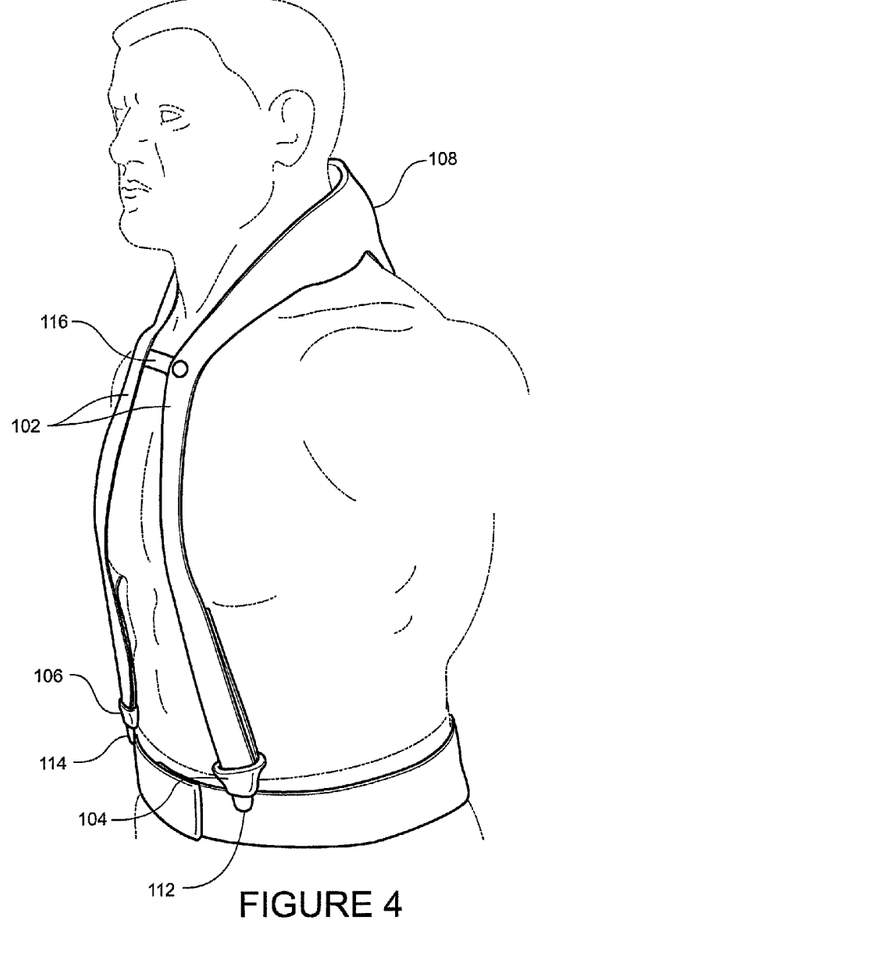
FIG. 4 is a perspective view of a neck cooling or neck heating apparatus applied to the neck of an individual according to one embodiment of the present invention.

FIG. 4 is a perspective view of the primary band (102) of FIG. 1 applied to the neck of an individual according to one embodiment of the present invention. Similar to that illustrated in FIG. 2, the first end (104) and the second end (106) of the primary band (102) are fastened to an article of clothing on the torso or waist of the individual by the first and second fasteners (112, 114), the article of clothing comprising the waistline of pants or shorts. The cross-member (116) couples sections of the primary band (102) on opposing sides of the neck cooling or neck heating region (108).

Figure 5:
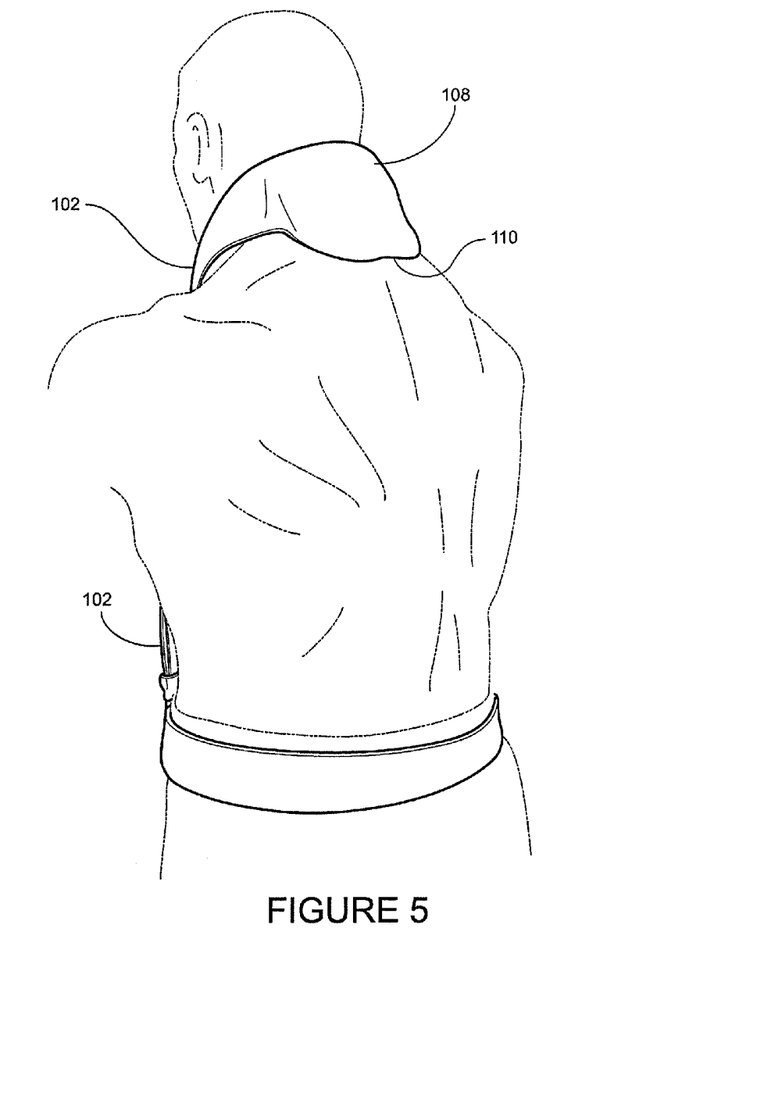
FIG. 5 is a perspective view of a neck cooling or neck heating apparatus applied to the neck of an individual according to one embodiment of the present invention.

FIG. 5 is a perspective view of the primary band (102) of FIG. 1 applied to the neck of an individual according to one embodiment of the present invention. As illustrated in FIG. 5, the neck cooling or neck heating region (108) of the primary band is positioned along the back of the individual's neck. A tissue cooling or tissue heating material (118) is coupled to the neck cooling or neck heating region (108) and resides between the skin of the individual and the primary band (102). The flange (110) extends down from the neck cooling or neck heating region (108) to reside under an article of clothing (not shown) being worn by the individual such as a shirt. The flange (110), in some embodiments, assists in keeping the neck cooling or neck heating region in the proper position.

Figure 6:
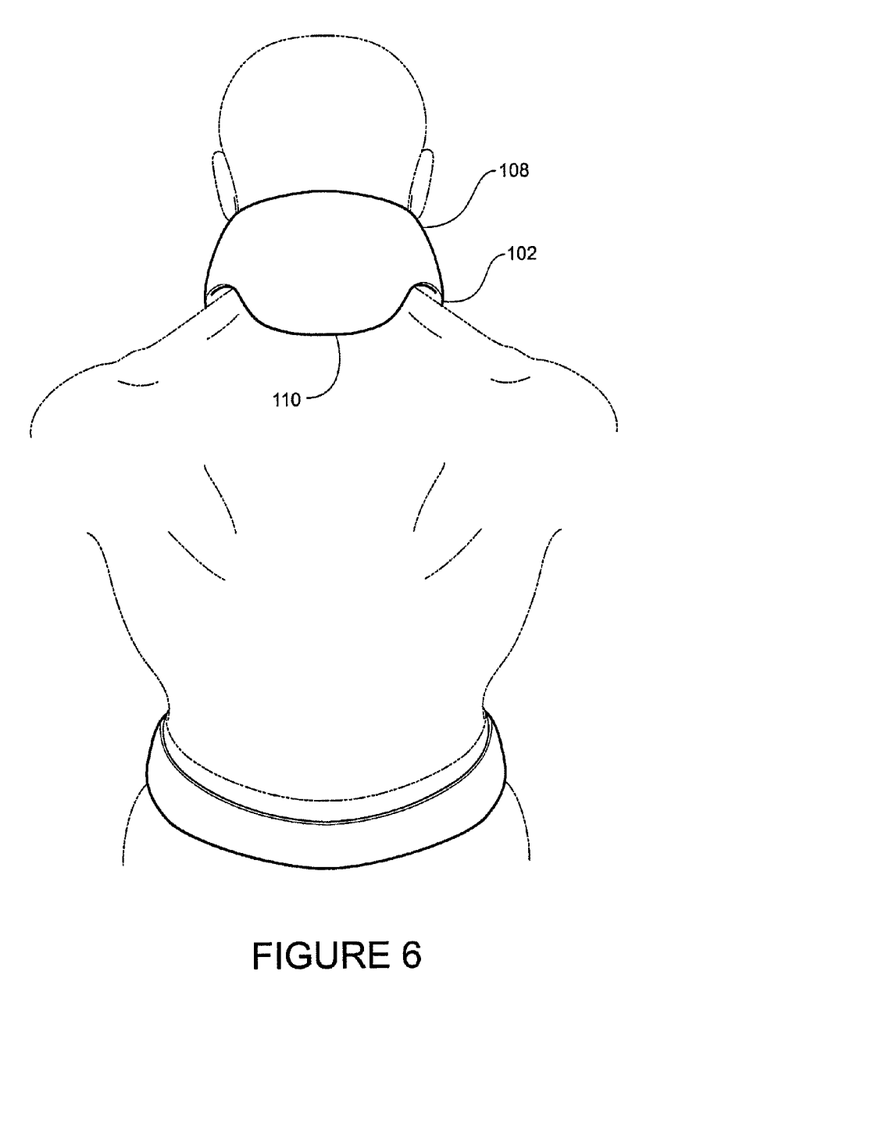
FIG. 6 is a back view of a neck cooling or neck heating apparatus applied to the neck of an individual according to one embodiment of the present invention.

FIG. 6 is a back view of the primary band (102) of FIG. 1 applied to the neck an individual according to one embodiment of the present invention. Similar to FIG. 5, the neck cooling or neck heating region (108) of the primary band is positioned along the back of the individual's neck. The flange (110) extends down from the neck cooling or neck heating region (108) to reside under an article of clothing (not shown) being worn by the individual such as a shirt.

In some embodiments, a neck apparatus of the present invention further comprises at least one secondary band, the secondary band comprising a first end and a second end, the first end coupled to the primary band and the second end coupled to an article of clothing on the torso or waist of an individual. A secondary band, in some embodiments, assists in further stabilizing the neck apparatus and maintaining the proper position of the neck cooling or neck heating region along an individual's neck. Referring once again to FIG. 6, a first end of a secondary band (122), in one embodiment, can couple to the flange (110) of the primary band (102) with the second end of the secondary band (122) coupled to the article of clothing on the individual.

Moreover, in some embodiments, a tissue cooling or tissue heating material can be coupled to the primary band in an area outside the neck cooling or neck heating region. In one embodiment, for example, a tissue cooling material or tissue heating material is coupled to a surface of the primary band between the neck cooling or neck heating region and the first or second ends of the band.

As illustrated in FIGS. 1-6, the neck apparatus of the present invention does not enclose the neck of an individual when in use. Moreover, the neck apparatus does not substantially restrict movement of the head, neck, back or arms, thereby permitting full freedom of movement. As a result of these advantageous properties, neck apparatus of the present invention find application in a wide variety of fields. Commercial laborers, for example, can utilize neck apparatus of the present invention while working to achieve relief from hot or cold working conditions. Additionally, athletes can use neck apparatus of the present invention during competition. As provided herein, in some embodiments, neck apparatus of the present invention does not enclose the neck allowing for use in contact sports. Furthermore, if a neck apparatus of the present invention is pulled by an external force, the apparatus can disengage from the clothing of an individual at the first or second ends of the primary band.

The primary band of a neck apparatus of the present invention can be constructed from any desired material. In some embodiments, the primary band is constructed of an elastomeric material including, but not limited to, rubber. In one embodiment, for example, the primary band is constructed of neoprene or styrene butadiene rubber (SBR)

In some embodiments, the primary band comprises a laminate material. In one embodiment, the primary band comprises a neoprene or SBR core covered by a fabric. Suitable fabrics for covering the neoprene core, in some embodiments, comprise polyamides (nylons), polyesters, spandex, fleece, natural fibers, UBL or other hook and loop materials. In some embodiments, the fabric is woven or non-woven. In some embodiments, the primary band of the neck apparatus comprises a neoprene or SBR core having a first side covered by UBL or other hook and loop material and the opposing side covered by a fabric comprising a polyamide, polyester, natural fibers, spandex or fleece material.

In some embodiments, exterior surfaces of the primary band further comprise logos or other advertising and/or information. In one embodiment, for example, surfaces of the primary band comprise the commercial logo or other information of a company whose workers utilize the neck apparatus. In another embodiment, surfaces of the primary band comprise the logo or other information of an athletic franchise whose players utilize the neck apparatus.

In some embodiments, the primary band can have any desired thickness not inconsistent with the objectives of the present invention. In some embodiments, the primary band has a thickness less than about 10 mm or less than about 5 mm. In other embodiments, the primary band of a neck apparatus has a thickness ranging from about 1 mm to about 5 mm. In a further embodiment, the primary band has a thickness greater than about 10 mm or less than about 1 mm.

In some embodiments, the primary band can have any desired width not inconsistent with the objectives of the present invention. In some embodiments, the primary band has a variable width. In one embodiment, for example, the width of the primary band at the first and/or second ends is less than the width of the primary band at the neck cooling or neck heating region. In some embodiments, the primary band has a width of at least 2.5 cm at the first and/or second end. In other embodiments, the primary band as a width of at least 3.8 cm at the first and/or second end.

In some embodiments, the primary band has a weight of less than about 0.5 pounds. In other embodiments, the primary band of a neck apparatus has a weight less than about 0.3 pounds or less than about 0.2 pounds. In a further embodiment, the primary band has a weight greater than about 0.5 pounds or less than about 0.2 pounds.

Tissue cooling and tissue heating materials suitable for use in neck apparatus of the present invention are known to those of skill in the art. In some embodiments, a tissue cooling or tissue heating material comprises a gel including, but not limited to, hydrogels. In another embodiment, a tissue cooling or tissue heating material comprises an aqueous solution having an appropriate solute solubilized or dispersed therein. In some embodiments, a tissue cooling or tissue heating material comprises a solid state material. Containers suitable for encapsulating tissue cooling or tissue heating materials are well known to one of skill in the art. In some embodiments, containers for tissue cooling or tissue heating materials comprise polymeric materials such polyolefins including polyethylene and polypropylene.

In some embodiments, tissue cooling or tissue heating materials are disposed in a linear array of individual compartments or containers. In another embodiment, tissue cooling or tissue heating materials are disposed in a two-dimensional array of individual compartments or containers. In one embodiment, at least one of the individual compartments of a two-dimensional array cooling or heating package can serve as a ridge or nub for facilitating the desired position of the neck cooling or heating apparatus on the neck of an individual. Moreover, in some embodiments, containers or compartments for tissue cooling or heating materials have a preformed shape substantially following the contours or curvature of the neck. In other embodiments, containers or compartments for tissue cooling or heating materials are flexible to conform to the contours or curvature of the neck.

In some embodiments, a tissue cooling or tissue heating material has a weight of less than about 0.5 pounds. In other embodiments, a tissue cooling or tissue heating material of a neck apparatus has a weight less than about 0.3 pounds or less than about 0.2 pounds. In a further embodiment, a tissue cooling or tissue heating material has a weight greater than about 0.5 pounds or less than about 0.2 pounds.

In another aspect, the present invention provides methods of heating or cooling the neck of an individual comprising providing a primary band comprising a first end, a second end and a neck cooling or neck heating region positioned between the first end and the second end, coupling a tissue cooling or tissue heating material to the neck cooling or neck heating region, positioning the neck cooling or neck heating material adjacent to the neck of an individual and coupling the first end and the second end of the primary band to an article of clothing around the torso or waist of the individual. In some embodiments, the primary band does not enclose the neck of the individual.

In some embodiments, a method of cooling or heating the neck of an individual further comprises tightening or loosening the primary band adjacent to the neck of the individual by coupling sections of the primary band on opposing sides of the neck cooling or neck heating region with a cross-member.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A neck cooling or heating apparatus comprising:
   a primary band comprising a first end, a second end and a neck cooling or neck heating region positioned between the first end and the second end, the neck cooling or neck heating region having coupled thereto a tissue cooling or tissue heating material,
   wherein the first end comprises a first fastener, and the second end comprises a second fastener, the first and the second fasteners adapted to couple to an article of clothing at the waist of an individual such that the primary band partially encircles the neck of the individual.

2. The neck cooling or heating apparatus of claim 1, wherein the first and the second fasteners are adapted to couple to the waistline of shorts or pants.

3. The neck cooling or heating apparatus of claim 1, further comprising a cross-member adapted to couple sections of the primary band on opposing sides of the neck cooling or neck heating region.

4. The neck cooling or heating apparatus of claim 3, wherein the cross-member is rotatable.

5. The neck cooling or heating apparatus of claim 4, wherein the cross-member rotates 360 degrees.

6. The neck cooling or heating apparatus of claim 3, wherein the cross-member is reversibly coupled to the primary band.

7. The neck cooling or heating apparatus of claim 1 further comprising at least one secondary band, the secondary band coupled to the primary band and the article of clothing on the torso or the waist of the individual.

8. The neck cooling or heating apparatus of claim 1, wherein the primary band comprises a polyamide, polyester, natural fibers or an elastomeric material or combinations thereof.

9. The neck cooling or heating apparatus of claim 8, wherein the elastomeric material comprises neoprene, styrene butadiene rubber or a combination thereof.

10. The neck cooling or heating apparatus of claim 1, wherein the primary band comprises an elastomeric core and woven fabric exterior.

11. The neck cooling or heating apparatus of claim 1, wherein a surface of the primary band further comprises one or more protrusions or ridges.

12. The neck cooling or heating apparatus of claim 1, wherein the first fastener or the second fastener engages the primary band by a loop through which the primary band is drawn.

13. A method of heating or cooling the neck of an individual comprising:
   providing a primary band comprising a first end, a second end and a neck cooling or neck heating region positioned between the first end and the second end;
   coupling a tissue cooling or tissue heating material to the neck cooling or neck heating region;
   positioning the tissue cooling or tissue heating material adjacent to the neck of an individual; and
   coupling the first end and the second end of the primary band to an article of clothing at the waist of the individual such that the primary band partially encircles the neck of the individual.

14. The method of claim 13 further comprising tightening or loosening the primary band adjacent to the neck of an individual by coupling sections of the primary band on opposing sides of the neck cooling or neck heating region with a cross member.

15. The method of claim 13, wherein the first end and the second end of the primary band are coupled to a waistline of shorts or pants.

16. The method of claim 13 further comprising adjusting tension in the primary band by passing the band through a loop of a first fastener of the first end.

17. The method of claim 13 further comprising adjusting tension in the primary band by passing the band through a loop of a second fastener of the second end.

* * * * *